United States Patent
De Klerk et al.

(10) Patent No.: US 8,293,215 B2
(45) Date of Patent: Oct. 23, 2012

(54) FLAVOUR MODULATING DERIVATIVE OF A CARBOXYLIC ACID AND A PURINE, PYRIMIDINE, NUCLEOSIDE, OR NUCLEOTIDE

(75) Inventors: Adri De Klerk, Amersfoort (NL); Marieke Baalbergen, Huizen (NL); Harry Renes, Lelystad (NL); Chris Winkel, Bussum (NL)

(73) Assignee: Givaudan Nederland Services B.V., Naarden (NL)

( * ) Notice: Subject to any disclaimer, the term of this patent is extended or adjusted under 35 U.S.C. 154(b) by 364 days.

(21) Appl. No.: 12/517,335

(22) PCT Filed: Dec. 13, 2007

(86) PCT No.: PCT/NL2007/050647
§ 371 (c)(1), (2), (4) Date: Jul. 6, 2009

(87) PCT Pub. No.: WO2008/072963
PCT Pub. Date: Jun. 19, 2008

(65) Prior Publication Data
US 2010/0074850 A1    Mar. 25, 2010

Related U.S. Application Data

(60) Provisional application No. 60/874,495, filed on Dec. 13, 2006.

(30) Foreign Application Priority Data

Dec. 13, 2006  (EP) .................................. 06125996

(51) Int. Cl.
| | |
|---|---|
| *A61K 8/18* | (2006.01) |
| *A61K 8/00* | (2006.01) |
| *A23L 1/22* | (2006.01) |
| *A23L 2/56* | (2006.01) |
| *C07H 19/167* | (2006.01) |
| *C07H 19/04* | (2006.01) |

(52) U.S. Cl. ....... 424/49; 426/535; 426/537; 536/27.81; 536/26.7

(58) Field of Classification Search .................... 424/49; 426/535, 537; 536/27.81, 26.7
See application file for complete search history.

(56) References Cited

U.S. PATENT DOCUMENTS

| | | | | |
|---|---|---|---|---|
| 6,808,716 | B2 * | 10/2004 | Yu et al. | 424/401 |
| 2002/0150936 | A1 * | 10/2002 | Beigelman et al. | 435/6 |
| 2008/0038428 | A1 | 2/2008 | Visser et al. | |
| 2008/0038430 | A1 | 2/2008 | Visser et al. | |

FOREIGN PATENT DOCUMENTS

| | | |
|---|---|---|
| EP | 0 576 227 A2 | 12/1993 |
| EP | 1 356 744 A | 10/2003 |
| WO | WO 2005/096843 | * 10/2005 |
| WO | WO 2005/096843 A | 10/2005 |
| WO | WO 2005/096844 A | 10/2005 |

OTHER PUBLICATIONS

Weenen, H., "Reactive intermediates and carbohydrate fragmentation in Maillard Chemistry", Food Chemistry, vol. 62, No. 4, pp. 393-401, Elsevier Science Publishers, LTD., 1998, Great Britain.

* cited by examiner

*Primary Examiner* — Marcos Sznaidman
(74) *Attorney, Agent, or Firm* — Curatolo Sidoti Co., LPA; Joseph G. Curatolo; Dinah H. Lewitan

(57) ABSTRACT

The present invention relates to the field of improving the flavor of foodstuffs, beverages, tobacco products, pharmaceutics and oral care products. More particularly, the present invention provides flavor modulating substances selected from the group represented by formula (I):

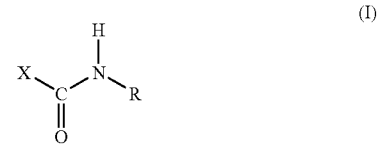

and edible salts thereof and edible esters thereof, which can advantageously be used for modulating the flavor of foodstuffs, beverages, tobacco products, pharmaceutics and oral care products. These flavor modulating substances can be used to impart desirable taste attributes in a wide variety of applications and products. In addition, the present flavor modulating substances are capable of modulating the taste and/or aroma impact of other, flavor imparting, substances contained within these same products, thereby improving the overall flavor quality of these products.

13 Claims, No Drawings

FLAVOUR MODULATING DERIVATIVE OF A CARBOXYLIC ACID AND A PURINE, PYRIMIDINE, NUCLEOSIDE, OR NUCLEOTIDE

CROSS REFERENCE TO RELATED APPLICATIONS

This application is a national stage application of International Application No. PCT/NL2007/050647, filed 13 Dec. 2007, which claims the benefit of European Patent Application Serial No. 06125996.6, tiled 13 Dec. 2006, and U.S. Patent Application Ser. No. 60/874,495, filed 13 Dec. 2006, from which applications priority is claimed, and which are incorporated herein by reference.

FIELD OF THE INVENTION

The present invention relates to the field of improving the flavour of foodstuffs, beverages, tobacco products, pharmaceutics and oral care products. More particularly, the present invention provides flavour modulating substances and compositions comprising them that can be used to improve and complement the impact of other flavour imparting substances. The present invention also encompasses the use of the aforementioned flavour modulating substances as well as foodstuffs, beverages, tobacco products, pharmaceutics and oral care products containing these substances.

BACKGROUND OF THE INVENTION

The flavour of foodstuffs and beverages consists of two parts: the aroma and the taste. In general what is perceived through the olfactory epithelium in the nasal cavity is referred to as 'aroma', whereas the term 'taste' is generally used to describe the sensory impact that is perceived via the mouth, especially the tongue. The flavour sensation experienced upon consumption, especially taste, provides the final analysis of food prior to ingestion thereof. Visual and olfactory (smell) signals already give a first indication but only after intake of the food into the mouth the final decision is made either to ingest or to reject the food. Sweet taste is usually a signal that the food is safe (appetising) leading to ingestion of the food. The 'reactions' to salt and umami are really dependent on the strength of the signal. Bitter and sour are usually repulsive taste sensations, leading to rejection. Temperature is another measure by which the food is judged just as well as aching sensations like capsaicin (hot pepper) and certain chemicals (like carbon dioxide).

In short, this means that taste is a very important and very complex system. Until recently most flavour research was focused towards aroma. Especially the last years a series of publications relating to molecules with a (positive) contribution to the taste of foodstuffs has emerged.

Such research has been stimulated significantly by the fact that quite some receptors which are involved in the different taste sensations have been characterized by now (J. Chandrashekar et al., Nature 444, 288 (2006)).

Another interesting aspect of taste is that it can have an impact on aroma. It was reported that people having artificially sweetened water in their mouth were significantly more sensitive to the smell of benzaldehyde than people having plain water in their mouth (P. Dalton et al, Nature Neurosci. 3, 431-432 (2000)).

Several screening systems have been described that make it possible to screen, in a short time, large series of molecules for their (modulating) effect on taste response (cf. WO 04/055048, GB 2396414, WO 01/77292 and US 2004/0072254).

Most research on taste modulation so far has been devoted to taste enhancement in savoury products. Several, mainly Japanese, publications describe umami molecules, i.e. alternatives to mono sodium glutamate (MSG) (H Suzuki et al, J Agric Food Chem 50, 313-318 (2002); K Shima et al, J Agric Food Chem 46, 1465-1468 (1998); Y Ueda et al, Biosc Biotech Biochem 61, 1977 (1997)).

In EP 1291342, a 'general taste enhancer' is disclosed that was reported to be suitable for enhancing sweetness as well.

In patent applications WO 97/04667 and WO 04/075633 tripeptides and amino acid condensates with lactic acid and succinic acid are described that have both their own taste as well as some enhancing properties. Alpha keto acids are reported to give body and mouthfeel to foodstuffs they are added to (U.S. Pat. No. 6,287,620).

Chlorogenic acids are claimed to enhance sweetness and to reduce bitterness (WO 02/100192).

Quite a bit of work has been devoted to find bitter taste suppressors (A. N. Pronin et al, Chemical Senses 29, 583-593 (2004); EP 1401500; P. A. Breslin, Trends in Food Science & Technology 7, 390-399 (1996)).

In sweet and beverage products, further examples of the importance of the gustative dimension of flavourings have been reported. These examples include taste attributes such as bitterness, tingling and cooling-freshness.

Bitterness is an essential aspect of some food flavours, among which chocolate taste. Purine alkaloids, like theobromine and caffeine, as well as amino acids and peptides have been known for a long time as bitter substances. In British patent no. GB 1420909 it is disclosed that the bitter flavour of cocoa can be reproduced using a combination of a purine alkaloid and an amino acid or an oligopeptide which 'produces a surprisingly more natural simultaneously bitter and astringent flavour note than either of these types of substances alone'.

Menthol, an important constituent of peppermint oil, has a strong impact on flavoured products not only because of its mint smell but also because it imparts a cooling and fresh taste. Next to mint flavoured products, it has been suggested to employ menthol in other types of flavour to impart a cool taste. US patent application no. US 2005/013846 for example discloses how menthol and derivatives thereof can be used as flavouring in water continuous spreadable acidified food products to obtain table spreads exhibiting a fresh, cool taste impression.

Similarly, cinnamic aldehyde and eugenol, constituents of cinnamon oil, are used in flavouring composition for confectionary products, not only for their smell but also because they impart a warm and tingling taste. The oral pungency of cinnamic aldehyde was described as burning and tingling by Cliff M and Heymann H (Journal of Sensory Studies 7, 279-290 (1992)). According to the same authors eugenol exhibits a long-lasting numbing effect. Cinnamon oil has been proposed as a taste improving flavouring. International patent application no. WO 90/06689 discloses that cinnamon oil, among other spice extracts, added to a minty flavour formulation, can be used to improve the long-lasting flavour of chewing-gum.

Vanillyl alcohol derivatives (e.g. vanillyl methyl or ethyl ether) are disclosed in patent US 2002/0013235 as having a strong pungent taste and warm feeling imparting effect. The same substances are described in patent JP 57082308 to be effective in increasing the refresh-feeling imparting effect of menthol. Vanillyl ethyl ether is more specifically disclosed as taste improving agent for beer in patent JP 20044229562. Substances from the same group such as vanillyl n-propyl ether are also disclosed in patent JP 57009729 as useful ingredients for salty taste.

Six different carbamic amides of vanillylamine, being structurally analogues to the pungent principle of cayenne pepper, have been tested for their properties of pungency (Lange et al.; J. Am. Chem. Soc., vol. 51, no. 6, 1911-1914 (1929). Vanillylurea, vanillylthiourea and phenylvanillylthiourea were however reported to be tasteless both as a dry powder and as an alcoholic or aqueous solution. Phenylvanillylthiourea, p-tolylvanillylthiourea and o-tolylvanillylthiourea were found to have the property of pungency but to a lesser degree than capsaicin.

Vanillyl amine and vanillyl acyl amides are also reported (U.S. Pat. No. 1,329,272) to be pungent molecules and can be used as substitutes or to fortify cayenne pepper for use in food and beverage to produce a hot or pungent taste.

N-(3-Acyloxy-2-benzylpropyl)-N-(4-hydroxy-3-methoxybenzyl) thiourea derivatives are disclosed as potent vanilloid receptor agonists and analgesics (Lee et al.; Bioorganic and medicinal chemistry 9, 9-12 (2001)). According to WO 2005/006881 these thiourea derivatives are also ligands of TRP V1 receptor, such that they would exhibit salty taste characteristics.

Derivatives of α-hydroxy carboxylic acids and purine or pyrimidines, such as GMP, AMP, CMP and IMP are disclosed in WO 2005/096843. According to said international patent application these substances are capable of modifying and complementing, the sensory impact of taste imparting substances. Thus, the present taste improving substances are advantageously applied in flavour compositions, foodstuffs, pharmaceutics, tobacco products, pharmaceutics and oral care products.

There is still a need for new substances having a positive contribution to the flavour, especially taste, of foodstuffs, beverages, tobacco products, pharmaceutics and/or oral care products they are incorporated in. One objective of the present invention is the provision of new substances and compositions that can complement and improve the impact of other flavour imparting substances, in particularly substances that have the ability to improve the impact of other flavour imparting substances at very low concentrations.

SUMMARY OF THE INVENTION

The present inventors have surprisingly found that substances selected from the group represented by formula (I):

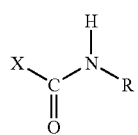

and edible salts thereof and edible esters thereof can advantageously be used for modulating the flavour of foodstuffs, beverages, tobacco products, pharmaceutics and oral care products.

The present flavour modulating substances can be used to impart desirable taste attributes in a wide variety of applications and products. In addition, the present flavour modulating substances are capable of modulating the taste and/or aroma impact of other flavour imparting substances contained within these same products, thereby improving the overall flavour quality of these products.

In spite of the aforementioned prior art disclosure teaching to use flavour modulating derivatives of purines or pyrimidines with α-hydroxy carboxylic acids, it has now been found that derivatives of purines or pyrimidines with carboxylic acids not containing an α-hydroxyl group constitute very potent flavour modulating substances. Moreover, as will be explained and illustrated hereafter, the present invention provides flavour modulating substances that can attain the desired effects at remarkably low dosages, when compared with said prior art flavour modulating substances.

Therefore, the present invention relates to these flavour modulating substances and to compositions comprising one or more of these substances. Furthermore, methods of improving the flavour of a product selected from foodstuffs, beverages, tobacco products, pharmaceutics and oral care products, as well as products comprising the present flavour modulating substances are provided by the invention.

DETAILED DESCRIPTION OF THE INVENTION

In one aspect of the invention flavour modulating substances according to formula (I) are provided as well as edible salts and esters thereof:

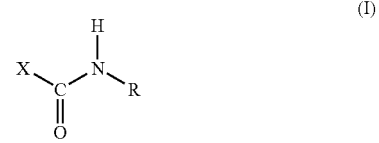

wherein X represents
  hydrogen;
  branched or unbranched, aliphatic or cyclic $C_1$-$C_{12}$ alkyl or $C_2$-$C_{12}$ alkenyl, each optionally substituted with one or more substituents selected from the group of oxo, hydroxyl, amine, thiol, lower thioalkyl, lower alkoxyl, guanidine and saturated or unsaturated heterocyclic moieties;
  a moiety represented by the formula —Z-Phe, wherein Z represents a covalent bond or a branched or unbranched saturated or unsaturated $C_1$-$C_6$ alkylene optionally substituted with one or more substituents selected from the group of oxo, hydroxyl, amine, and lower alkoxyl and wherein Phe represents phenyl, optionally substituted with one or more substituents selected from hydroxyl, amine and lower alkoxyl;
  a moiety represented by the formula —Y—CO—NHR, wherein Y represents branched or unbranched saturated or unsaturated $C_1$-$C_{12}$ alkylene, optionally substituted with one or more substituents selected from the group of oxo, hydroxyl, amine, thiol, lower thioalkyl, lower alkoxyl and lower carboxyl;
with the proviso that X does not represent a moiety wherein the α carbon atom is substituted with a hydroxyl group;
and wherein R represents (i) a moiety comprising a six membered heterocyclic ring, comprising at least two nitrogen atoms, which heterocyclic ring is optionally further substituted with one or more substituents selected from the group of amino; hydroxyl; oxo; alkyl; ribose and deoxyribose and phosphate esters of ribose and deoxyribose; or (ii) a moiety comprising a bicyclic fused ring system comprising a five membered heterocyclic ring and a six membered heterocyclic ring, each ring comprising at least two nitrogen atoms, and each ring being optionally further substituted with one or more substituents selected from the group of amino; hydroxyl; oxo; alkyl; ribose and deoxyribose and phosphate esters of ribose and deoxyribose.

The term "lower" as used herein in connection to the terms "alkoxyl" and "thioalkyl" means that the moiety concerned comprises a carbon chain portion of not more than six carbon atoms, preferably of not more than four carbon atoms, most preferably of not more than three carbon atoms.

The present inventors have found that the above-mentioned flavour modulating substances are very useful flavour ingredients which, particularly in the presence of other flavour imparting substances, are capable of imparting highly appreciated taste sensations to the products in which they are incorporated, specifically "cooling", "pungent", "sharp", "hot" "tingling", "bite", "burning", "warm", "alcohol-like", "continuity", "complexity", "expanding", "salty", "umami" and/or "long lasting". Because of this, the present substances can be employed to improve the flavour, especially taste (including "mouthfeel"), of foodstuffs, beverages, tobacco products, pharmaceutics and oral care products.

The flavour modulating substances of the present invention as such are capable of imparting highly desirable taste attributes. In addition, it has been found that the flavour modulating substances according to the invention are capable of complementing and modifying the sensory impact of other, flavour imparting, substances, contained in the aforementioned products, including complementing and modulating "alcohol sensation", "bitterness", "hot taste sensation", "cold taste sensation", "carbonation effects", and/or "salt taste impact". Without wishing to be bound by any theory, the findings of the present invention seem to suggest that the presence of sodium chloride and/or mono sodium glutamate greatly affects the aforementioned properties, in that the above-mentioned effects are attained at much lower concentrations of the flavour modulating substances in the presence of NaCl and/or MSG.

Throughout this document the term "flavour" is used to describe the sensory impact that is perceived via the mouth, especially the tongue, and the olfactory epithelium in the nasal cavity. The term "complementing and modifying the sensory impact" as used herein refers to the capability of the present compositions or substances to alter the taste and/or aroma impact of other, flavour imparting, substances present within the same product, with the proviso that this change in taste impact is not caused by the flavour contribution of said composition or substance per se, but instead that it mainly results from the combined effect of on the one hand the present flavour modulating composition or substance and on the other hand the other flavour imparting substance(s). The present flavour modulating substances combine the capability of modulating the taste and/or aroma of other, flavour imparting, substances and a taste contribution of their own. The favourable impact of the present flavour modulating substances is believed to be the result of the combination of these two effects. Because the flavour modulating substances according to the invention are not particularly volatile, they do not produce a strong aroma impact, even though they can affect the aroma impact of other flavour imparting substances. Here the term "aroma" refers to the aspect of flavour that is perceived through the olfactory epithelium. Because of the low volatility of the present flavour modulating substances it is believed that the advantageous properties of these substances are somehow associated with the impact that these substances have on the sensory receptors located within the mouth.

In one embodiment of the invention, X represents hydrogen, such that the moiety X—CO— represents the residue of formic acid.

In another equally preferred embodiment of the invention, X represents branched or unbranched, aliphatic or cyclic $C_1$-$C_{12}$ alkyl or $C_2$-$C_{12}$ alkenyl, each optionally substituted with one or more substituents selected from the group of oxo, hydroxyl, amine, thiol, lower thioalkyl, lower alkoxyl, guanidine and saturated or unsaturated heterocyclic moieties.

Particularly satisfying results are obtained with flavour modulating substances as defined herein before wherein X represents branched or unbranched $C_1$-$C_8$ alkyl or $C_2$-$C_8$ alkenyl each optionally substituted with one or more substituents selected from the group of oxo, hydroxyl, amine, thiol, lower thioalkyl, lower alkoxyl, guanidine, imidazole, indole and pyrrolidine. Even more preferably X represents branched or unbranched $C_1$-$C_8$, preferably $C_1$-$C_4$, more preferably $C_1$-$C_2$ alkyl; X represents branched or unbranched $C_1$-$C_5$ α-amino alkyl, optionally substituted with one or more substituents selected from oxo, hydroxyl, amine, thiol, lower thioalkyl, lower alkoxyl, guanidine, imidazole, indole and pyrrolidine; X represents $C_1$-$C_2$ alkyl substituted with an oxo substituent; or X represents saturated or unsaturated $C_2$-$C_6$ carboxyl, optionally substituted with a substituent selected from the group of oxo and lower carboxyl, or $C_2$-$C_4$ α-amino carboxyl. Most prefereably the moiety X—CO— represents the residue of acetic acid, propionic acid, butyric acid, pentanoic acid, hexanoic acid, heptanoic acid, octanoic acid, pyruvic acid, oxalic acid, succinic acid, glutaric acid, fumaric acid, maleic acid, adipic acid, citric acid, oxalacetic acid, aspartic acid, glutamic acid glycine, alanine, arginine, asparagine, cysteine, glutamine, histidine, isoleucine, leucine, lysine, methionine, proline, serine, threonine, tryptophan, or valine.

In another preferred embodiment substances as defined herein before are provided wherein X represents branched or unbranched $C_1$-$C_{12}$ alkyl or $C_2$-$C_{12}$ alkenyl, preferably $C_1$-$C_8$ alkyl or $C_2$-$C_8$ alkenyl, each optionally substituted with one or more substituents selected from the group of oxo, hydroxyl, amine, thiol, lower thioalkyl and lower alkoxyl. Even more preferably X represents branched or unbranched $C_1$-$C_8$, more preferably $C_1$-$C_4$, more preferably $C_1$-$C_2$ alkyl; X represents $C_1$-$C_2$ alkyl substituted with an oxo substituent; or X represents saturated or unsaturated $C_2$-$C_6$ carboxyl, optionally substituted with a substituent selected from the group of oxo and lower carboxyl, or $C_2$-$C_4$ α-amino carboxyl. Most preferably the moiety X—CO— represents the residue of acetic acid, propionic acid, butyric acid, pentanoic acid, hexanoic acid, heptanoic acid, octanoic acid, pyruvic acid, oxalic acid, succinic acid, glutaric acid, fumaric acid, maleic acid, adipic acid, citric acid and oxalacetic acid.

In another equally preferred embodiment of the invention X represents -Phe, i.e. Z represents a covalent bond. Particularly satisfying results are obtained with flavour modulating substances as defined herein before wherein -Phe represents phenyl substituted with 1-3 substituents selected from hydroxyl, amino and methoxyl. Most prefereably the moiety X—O— represents the residue of benzoic acid, gallic acid, vanillic acid or anthranilic acid.

In yet another, equally preferred embodiment of the invention, Z represents saturated or unsaturated $C_1$-$C_4$ alkylene optionally substituted with one or more substituents selected from the group of oxo, hydroxyl, amine, and lower alkoxyl. Particularly satisfying results are obtained with flavour modulating substances as defined herein before wherein Z represents unsaturated $C_2$-$C_4$ alkylene and -Phe represents phenyl optionally substituted with 1-3 substituents selected from hydroxyl and methoxy, or wherein Z represents a $C_1$-$C_2$ α-amino alkylene, optionally substituted with 1-3 hydroxyl groups. Most preferably the moiety X—O— represents the residue of cinnamic acid, caffeic acid, ferulic acid, phenylalanine or tyrosine.

In yet another, equally preferred embodiment of the invention, X represents a moiety represented by the formula —Y—CO—NHR, wherein Y represents branched or unbranched saturated or unsaturated $C_1$-$C_{12}$ alkylene, optionally substituted with one or more substituents selected from the group of oxo, hydroxyl, amine, thiol, lower thioalkyl, lower alkoxyl and lower carboxyl. Particularly satisfying results are obtained with flavour modulating substances as defined herein before wherein X represents a moiety represented by the formula —Y—CO— NHR, wherein Y represents saturated or unsaturated $C_1$-$C_8$ alkylene, optionally substituted with one or more substituents selected from the group of oxo, hydroxyl, amine and lower carboxyl. According to said embodiment, the flavour modulating substance is preferably a derivative of a di or tri carboxylic acid with two moieties represented by the formula —NHR, said dicarboxylic acid most preferably being selected from the group of oxalic acid, succinic acid, glutaric acid, fumaric acid, maleic acid, adipic acid, citric acid, oxalacetic acid, aspartic acid or glutamic acid.

In one embodiment of the invention, it is preferred that the moiety R represents a purine or a pyrimidine radical that is substituted with a pentose monosaccharide unit, preferably ribose or deoxyribose, or a phosphate ester thereof, such that the —NRH moiety represents the residue of a nucleoside or nucleotide.

In a particularly preferred embodiment, the moiety —NRH represents the residue of a purine radical, a pyrimidine radical, a nucleotide or nucleoside selected from the group of cytosine, guanine, adenine, guanosine, adenosine, cytidine, guanosine 5'-monophosphate (GMP), adenosine 5'-monophosphate (AMP), or cytidine 5'-monophosphate (CMP), most preferably the residue of GMP.

In an even more preferred embodiment the invention relates to flavour modulating substances selected from the group of N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, N-acetyl AMP, N-formyl AMP, N-propanoyl AMP, N-butanoyl AMP, N-pentanoyl AMP, N-hexanoyl AMP, N-heptanoyl AMP, N-octanoyl AMP, N-oxalyl AMP, N-succinyl AMP, N-glutaryl AMP, N-fumaryl AMP, N-maleyl AMP, N-adipyl AMP, N-citryl AMP, N-galloyl AMP, N-oxalacetyl-AMP, N-feruloyl AMP, N-pyruvyl AMP, N-benzoyl AMP, N-vanilloyl AMP, N-anthranoyl AMP, N-caffeoyl AMP, N-cinnamoyl AMP, N-acetyl CMP, N-formyl CMP, N-propanoyl CMP, N-butanoyl CMP, N-pentanoyl CMP, N-hexanoyl CMP, N-heptanoyl CMP, N-octanoyl CMP, N-oxalyl CMP, N-succinyl CMP, N-glutaryl CMP, N-fumaryl CMP, N-maleyl CMP, N-adipyl CMP, N-citryl CMP, N-galloyl CMP, N-oxalacetyl-CMP, N-feruloyl CMP, N-pyruvyl CMP, N-benzoyl CMP, N-vanilloyl CMP, N-anthranoyl CMP, N-caffeoyl CMP, N-cinnamoyl CMP, edible salts thereof and edible esters thereof. Even more preferably the invention relates to flavour modulating substances selected from the group of N-acetyl GMP, N-formyl GMP, N-propanoyl GMP, N-butanoyl GMP, N-pentanoyl GMP, N-hexanoyl GMP, N-heptanoyl GMP, N-octanoyl GMP, N-oxalyl GMP, N-succinyl GMP, N-glutaryl GMP, N-fumaryl GMP, N-maleyl GMP, N-adipyl GMP, N-citryl GMP, N-galloyl GMP, N-oxalacetyl-GMP, N-feruloyl GMP, N-pyruvyl GMP, N-benzoyl GMP, N-vanilloyl GMP, N-anthranoyl GMP, N-caffeoyl GMP, N-cinnamoyl GMP, edible salts thereof and edible esters thereof. Most preferably the invention relates to flavour modulating substances selected from the group of N-acetyl GMP, edible salts thereof and edible esters thereof.

As used herein the term 'edible esters thereof' refers to a derivative of a flavour modulating substance of the invention and an acid or alcohol formed by reaction of said acid or alcohol with a hydroxyl group or carboxyl group, respectively, that is present in said flavour modulating substance, said derivative being suitable for human consumption, i.e. being non-toxic, and having flavour modulating properties in accordance with was has been explained herein before.

The term "edible salt", as used herein, refers to a salt that is generally considered suitable for human consumption, particularly a non-toxic salt. Acceptable salts include base addition salts and acid addition salts of the corresponding free acid. These salts typically may be prepared by conventional means from the free acid of the present flavour modulating substances. Illustrative base addition salts include metallic salts and organic salts. Metallic salts include alkali metal salts, such as sodium and potassium salts, alkaline earth metal salts, such as calcium and magnesium salts. Organic salts include salts made from secondary, tertiary and quaternary amines such as diethylamine, triethylamine, ethanolamine, diethanolamine, and salts made from cationic amino acids such as arginine, lysine and histidine. Examples of suitable acid addition salts include hydrochloride, phosphate, hydrogen phosphate, acetate, aspartate, ascorbate, citrate, gluconate, lactate, succinate, tartrate, etc.

A second aspect of the invention relates to flavouring compositions comprising at least 60 ppt of one or more of the present flavour modulating substances selected from the group of substances represented by formula (I), edible salts thereof and edible esters thereof, as well as at least 0.1 wt % of one or more flavouring substances. Particularly preferred examples of the flavour modulating substances in accordance with the invention are as defined herein before. Typically the flavour compositions of the present inventions comprise the one or more flavour modulating substances in an amount of less than 10,000 ppm.

The term "comprising" whenever used in this document is intended to indicate the presence of stated features, integers, steps, components, but not to preclude the presence or addition of one or more other features, integers, steps, components or groups thereof.

As used herein the term "flavour imparting substance" is meant to encompass any food grade substance that is capable of imparting a detectable flavour impact, typically at concentrations below 1 wt. %, more preferably below 0.1 wt. %. Suitable examples of flavouring substances include alcohols, aldehydes, ketones, esters, ethers, acetates, nitriles, terpene hydrocarbons, nitrogenous or sulphurous heterocyclic compounds and essential oils, and said flavouring substances can be of natural or synthetic origin. Many of these are listed in reference texts such as the book by S. Arctander, Perfume and Flavor Chemicals, 1969, Montclair, N.J., USA, or its more recent versions, or in other works of a similar nature, as well as in the abundant patent literature in the field of flavours. It will be clear to the skilled person that the type of flavouring substance added would entirely depend on the type of product to which the composition is added.

The expressions "ppt", "ppb" and "ppm" as used herein refer to amounts expressed in, respectively, parts per trillion, 1 ppt corresponding to 1 ng/kg; parts per billion, 1 ppb corresponding to 1 μg/kg; and parts per million, 1 ppm corresponding to 1 mg/kg. These expressions are common terms in the art of flavours and fragrances and understood by the skilled person as having the meaning given here.

Preferably, the flavour composition contains at least 120 ppt, more preferably at least 300 ppt, still more preferably at least 1.2 ppb, most preferably at least 6 ppb of the present flavour modulating substances. In another preferred embodiment the composition contains less than 1,000 ppm, preferably less than 200 ppm, more preferably less than 50 ppm and most preferably less than 10 ppm of the present flavour modulating substances.

In a preferred embodiment the flavour composition according to the invention comprises a flavouring substance in an amount of at least 0.5 wt %, preferably at least 1 wt %, based on the total weight of the composition.

Typically, in the present flavour composition the taste modulating substances and flavouring substances as defined herein before are employed in a weight ratio of less than 1:50, preferably less than 1:100, more preferably less than 1:1,000 and most preferably in a weight ratio of less than 1:10,000.

The flavour composition according to the present invention may suitably be prepared in the form of a liquid, a paste or a powder. In a particularly preferred embodiment the flavour composition is a free flowing powder. Typically the present flavouring compositions further comprise at a flavour carrier material. As used herein, the term flavour "carrier material" encompasses a bulk material that is practically neutral from a flavour point of view, i.e. that does not significantly alter the organoleptic properties of flavouring ingredients. Said carrier may be a liquid or a solid. Suitable examples of liquid carriers include emulsifying systems, i.e. a solvent and a surfactant system, or a solvent commonly used in perfumery or flavours. Suitable limiting examples of solvents commonly used in flavours, one can cite compounds such as propylene glycol, triacetine, triethyl citrate, benzylic alcohol, ethanol, vegetal oils or terpenes. Examples of solid carriers include absorbing gums or polymers or encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or the materials cited in reference texts such as H. Scherz, Hydrokolloids: Stabilisatoren, Dickungs-und Gehermittel in Lebensmittel, Band 2 der Schriftenreihe Lebensmittelchemie, Lebensmittelqualitat, Behr's VerlagGmbH & Co., Hamburg, 1996.

Typical examples of flavour compositions according to the present invention include savoury flavourings, dairy flavourings, sour flavourings, sweet flavourings and mint flavourings, savoury and dairy flavourings being particularly preferred.

The present flavour composition advantageously contains at least 0.5 wt % of a processed flavour, in particular a processed flavour that contains cystein derived Maillard reaction products.

The present flavour compositions defined herein before are typically prepared by compounding one or more of the flavouring substances with a solution containing at least 10 ppb, preferably at least 50 ppb of the present flavour modulating substances or edible salt thereof. The preparation of flavour compositions containing said flavour modulating substances in extremely low concentrations is facilitated by compounding a solution of these flavour modulating substances with one or more of the flavouring substances. In particular, this approach offers the advantage that it enables accurate dosing of the flavour modulating substances. Typically, the solution containing the flavour modulating substances and/or edible salts thereof is compounded with the remainder of the flavour composition in a weight ratio of less than 1:1, preferably of less than 1:5 and most preferably of less than 1:10. It is noted that the solution may suitably contain one or more flavouring substances, especially highly potent flavouring substances. The solvent employed in the solution can be any foodgrade solvent that is allowed for use in flavour compositions. Examples of suitable solvents include ethanol, water, triglyceride oil and propylene glycol.

A third aspect of the invention relates to a product selected from the group of foodstuffs, beverages, pharmaceutics, oral care products and tobacco products, preferably from the group of foodstuffs and beverages, said product comprising a flavour modulating amount of one or more of the present flavour modulating substances selected from the group of substances represented by formula (I), edible salts thereof and edible esters thereof, as defined herein before.

Typically, the present product comprises at least 0.3 ppt of one or more of the present flavour modulating substances. More preferably, products of the invention comprise at least 0.6 ppt, more preferably at least 1.5 ppt, most preferably at least 30 ppt of one or more of the flavour modulating substances according to formula (I) or edible salts thereof. Typically, the aforementioned products preferably contain the flavour modulating substances in a concentration of not more than 5 ppm, preferably of not more than 2.5 ppm, more preferably of not more than 1 ppm, still more preferably of not more than 250 ppb, most preferably of not more than 50 ppb. The precise level in which the present substances are incorporated depends on the nature of the flavour modulating substance(s) and the nature of the product, as will be clear to the skilled person, and as will be illustrated in the examples.

Preferred examples of foodstuffs according to the present invention include soups, sauces, stocks, bouillons, snacks, cheese products, dressings, seasonings, margarines, shortenings, bread, pastry and noodles.

A preferred example of a beverage according to the present invention includes a dairy drink.

The term 'tobacco products', as used herein, refers to any type of tobacco product for smoking as well as for non-smoking applications. It is furthermore noted that tobacco-like products are available for both smoking and non-smoking applications. The use of the present flavour modulating substances in tobacco substitutes is also encompassed by the present invention.

Suitable examples of oral care products according to the present invention include toothpastes, mouthwashes, dental floss, anti-plaque and anti-gingivitis compositions.

Most preferably, in accordance with the invention the product is selected from the group of foodstuffs and beverages.

Yet, according to another preferred embodiment of the invention the foodstuff or beverage contains sodium chloride and/or monosodium glutamate. As explained herein before, the presence of NaCl and MSG greatly increases the flavour modulating potency of the substances of the invention. Most preferably the foodstuff or beverage contains at least 0.01 wt % of NaCl and/or 0.001 wt % of MSG.

A fourth aspect of the invention relates to a method of improving the flavour of a product selected from the group of foodstuffs, beverages, pharmaceutics, oral care products and tobacco products, said method comprising incorporating in said product a flavour modulating amount of one or more of the present flavour modulating substances selected from the group of substances represented by formula (I), edible salts thereof and edible esters thereof, as defined herein before.

Particularly Preferred examples of the flavour modulating substances, products and amounts in accordance with the invention are as described here above.

A fifth aspect of the invention relates to the use of one or more flavour modulating substances selected from the group of substances represented by formula (I), edible salts thereof and edible esters thereof for improving the flavour of a product selected from the group of foodstuffs, beverages, pharmaceutics, oral care products and tobacco products.

Preferred examples of the flavour modulating substances, products and amounts in accordance with the invention are as described here before.

As mentioned here above, the present flavour modulating substances are particularly suitable for modulating, especially improving and/or complementing salty taste impact, umami impact, sweet taste impact, complexity and continuity. Hence a preferred embodiment of the invention relates to the afore defined use for improving and/or complementing salt taste impact, umami impact, sweet taste impact, flavour complexity and flavour continuity. Complexity and continuity are terms commonly used in the art of flavouring to denote the flavour qualities also referred to as "fullness and richness" and "long-lasting and expanding" respectively.

A sixth aspect of the invention relates to a process of producing a flavour modulating substance represented by formula (I), an edible salts thereof or an edible ester thereof, said process comprising reacting a properly protected amine represented by the formula $NH_2R$, wherein R has the same meaning as defined herein before in relation to formula (I) with an activated derivative of a carboxylate represented by formula (III):

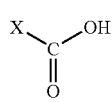

(II)

wherein X has the same meaning as defined herein before in relation to formula (I), typically by heating combinations of such starting materials. As will be understood by the skilled person, properly protected, as used herein, means that all reactive groups of the molecule are protected by protective groups, which are known in the art, except the primary amine that is to be derivatised with the carboxylic acid. The term activated carboxylic acid, typically encompasses (mixed) anhydrides, esters, acid chlorides or acid bromides of the carboxylic acid, as will be recognised by the skilled person. It was found that in order to obtain the derivative of a carboxylic acid and a nucleotide according to formula (I), it is typically preferred to first prepare the derivative of the corresponding nucleoside and prepare the phosphate ester thereof in a second step, as will be shown in the appending examples. The present method of preparing flavour modulating substances comprises processes that make use of conventional reactions. Preferably said reaction is performed by heating under reflux the reactants in an organic solvent or a mixture of organic solvents, e.g. DMF/pyridine, for a period of between 0.1-10 hours. According to the present processes the reaction products are typically obtained as a precipitate and can be isolated by evaporating the solvent and optionally further purified using any of the techniques known by the skilled person, such as chromatography and crystallization.

According to another particularly preferred embodiment of the present process, a reaction of the purine, pyrimidine, nucleotide and/or nucleoside with a carboxylate is carried out in the presence of a carbohydrate source. Typically, the reaction is carried out by first preparing a mixture of (i) one or more amines represented by the formula $NH_2R$; (ii) one or more of the carboxylates; and the carbohydrate source, followed by heating said mixture. Preferably, the carbohydrate source is incorporated in the mixture in a concentration of at least 0.5 wt. %, more preferably of at least 1 wt. %.

In a particularly preferred embodiment of the present process a process flavour preparation, preferably a Maillard flavour preparation, is produced by heating a mixture of (i) a carbohydrate source; (ii) a nitrogen source, said nitrogen source comprising 0.5-100 wt %, preferably 1-50 wt %, most preferably 2-25 wt %, of the one or more purines, pyrimidines, nucleotides and/or nucleosides and (iii) one or more of the carboxylates represented by formula (II) above.

The combination of nitrogen source and carbohydrate source preferably represents at least 1 wt. % of the mixture before it is heated. More preferably, said mixture represents at least 5 wt. % and most preferably at least 15 wt. % of the mixture. Maillard flavour preparations obtained by said process will typically comprise one or more of the present flavour modulating substances. Thus, the aforementioned process preferably yields a Maillard flavour preparation comprising effective amounts of one or more substances according to formula (I) or salts thereof.

The term "Maillard flavour preparation" as used herein refers to a flavour preparation which is obtained by heating a mixture of ingredients including a nitrogen source, preferably amino nitrogen, and a carbohydrate source, preferably a reducing sugar. The terms "process flavour" or "reaction flavour" which are used interchangeably herein refer to compositions or products obtained by heat processing together a protein nitrogen source and a carbohydrate source, at a temperature, preferably, not exceeding 180° C. In the present process it is particularly preferred to heat the combination of carbohydrate source, nitrogen source and liquid phase to a temperature of between 60-180° C., even more preferably between 100-140° C. According to a preferred embodiment the heating is carried out for a period of 0.1-8 hours, preferably of 0.5-7 hours.

According to a particularly preferred embodiment the carboxylates are present in the mixture as a continuous liquid phase. The term "liquid" as used herein in relation to the continuous liquid phase refers to the fact that, especially under the heating conditions employed, the continuous phase exhibits fluid or flowing behaviour. Furthermore, it should be understood that the term liquid embraces emulsions and suspensions.

According to a preferred embodiment of the present invention the process is performed in a continuous liquid phase containing at least 40 wt %, more preferably at least 45 wt %, most preferably at least 50 wt % of the carboxylate. The present continuous liquid phase advantageously comprises water in an amount sufficient to liquefy the carboxylate, e.g. in an amount of at least 2 wt. %, even more preferably at least 5 wt. %. It is preferred that the amount of water does not exceed 70 wt. %, based on the total weight of the continuous liquid phase, preferably it does not exceed 60 wt. %, more preferably it does not exceed 45 wt. %.

Preferably the said continuous liquid phase comprises an carboxylic acid such as formic acid, acetic acid, propionic acid, butyric acid, pentanoic acid, hexanoic acid, heptanoic acid, octanoic acid, oxalic acid, succinic acid, glutaric acid, fumaric acid, maleic acid, adipic acid, citric acid, pyruvic acid, oxalacetic acid, cinnamic acid, caffeic acid, benzoic acid, gallic acid, vanillic acid, anthranilic acid, ferulic acid or a salt thereof. In a particularly preferred embodiment the carboxylic acid component is acetic acid.

The carbohydrate source can be any type conventionally used in the field of process flavours and Maillard flavour preparations. Preferably the carbohydrate source comprises a reducing sugar. Non-limiting examples include ribose, xylose, glucose, fructose, rhamnose, lactose, maltose and sucrose.

The present "nitrogen source", besides the substances represented by the aforementioned formula NH—R, may furthermore comprise a protein nitrogen source, autolyzed yeasts, peptides, amino acids and/or their salts, decarboxylated amino acids, salts thereof and mixtures thereof. In a particularly preferred embodiment of the invention the nitrogen source comprises a yeast extract, in particular a yeast extract comprising GMP in amounts ranging from 1 to 25 wt %, preferably from 2 to 20 wt %. Suitable examples of such yeast extracts include Aromild, containing approximately 10 wt % of GMP, Umamex I, containing approximately 15 wt % of GMP, Umamex II, containing approximately 4.4 wt % of GMP and/or YEP 99, containing approximately 2.5 wt % of GMP. Aromild is a commercially available yeast extract sold by Kohjin. Umamex I and II and YEP 99 are commercially available from Kerry Biosciences. In a preferred embodiment of the present process the nitrogen source and the carbohydrate source are employed in a weight ratio within the range of 1:20 to 20:1. In another preferred embodiment the employed weight ratio of carboxylates and/or salts thereof relative to the combination of carbohydrate source and nitrogen source is within the range of 1:1 to 20:1, more preferably within the range of 2:1 to 10:1.

The present invention will now be further illustrated in the following examples, which are not intended to limit the scope of the invention as described herein before and/or as defined in the claims.

EXAMPLES

Example 1

Preparation of N-acetyl-guanosine

A solution of 11.3 g guanosine in DMF/pyridine/acetic anhydride (50 ml each) was heated under reflux (116° C.) for 3 hours. All liquids were removed by distillation (100° C./30 mbar), and the residue was dissolved in 80 ml methylenechloride. The methylenechloride solution was washed twice with a 1M hydrochloric acid solution and twice with a saturated sodiumbicarbonate solution. Solvent was evaporated and the residue was taken up in a mixture of 50 ml THF, 40 ml methanol and 35 ml of water. This solution was treated with a solution of 1.6 g sodiumhydroxide in 4 ml of water. The mixture was left to stand at room temperature for 20 minutes. 5 ml Of acetic acid was added and the solution was concentrated to approximately 80 ml. Some isopropanol was added and the solution was cooled to −20° C. N-acetyl-guanosine was filtered and dried in the vacuum oven at 50° C./10 mbar to yield 4 g of a light brown powder. Using $^1$H NMR spectroscopy, it was demonstrated that the product was N-acetyl-guanosine.

Example 2

Preparation of N-acetyl-GMP 1.8 g Phosphoryl chloride was mixed with 7 ml of trimethylphosphate and cooled to −10° C. under a nitrogen atmosphere. To this solution 1.6 g acetyl-guanosine (example 1) was added in small portions and under stirring keeping the temperature below −10° C. The mixture was stirred for 3 hours keeping the temperature below −5° C. The reaction mixture was quenched by pouring the solution into 300 ml of ice/water and subsequently the pH was adjusted to 2 with sodiumhydroxide 33%. The solution was percolated on a column (diameter=3 cm) containing 30 g activated charcoal, washed with water to remove salts and eluted with an ethanol/water/28% NH$_4$OH (50/48/2) mixture consisting of 100 ml ethanol, 100 ml water and 4 ml of ammonia 28%. The eluate was evaporated to dryness. The half solid residue was taken up in ethanol/methyl tert. butyl ether and the solids were filtered and dried in the vacuum oven at 60° C./10 mbar to yield 0.8 g of N-acetyl-GMP. Using $^1$H NMR spectroscopy, it was confirmed that the product was N-acetyl-GMP.

Example 3

Six aqueous solutions were prepared:

A. 0.5% salt and 0.05% MSG
B. 1 ppm GMP dissolved in solution A
C. 0.2 ppm of a process flavour containing 0.3% lactoyl-GMP dissolved in solution A
D. 0.6 ppb lactoyl-GMP dissolved in solution A
E. 1 ppb acetyl-GMP in solution A
F. 30 ppb acetyl-GMP in solution A The solutions were tasted by a professional sensory panel.
Solution A was described as: "salty"
Solution B was described as: "sweet", "lingering umami"
Solution C was described as: "sweet", "lingering umami", "stronger than B"
Solution D was described as: "sweet", "lingering umami", "more salivating", "stronger than C"
Solution E was described as: "salivating", "salty", "stronger than D"
Solution F was described as: "salivating", "salty", "stronger than E"

Example 4

Three aqueous solutions were prepared:

A. 0.5% salt and 0.05% MSG
B. 0.6 ppb lactoyl-GMP dissolved in solution A
C. 0.1 ppt acetyl-GMP in solution A
D. 10 ppt acetyl-GMP in solution A The solutions were tasted by a professional sensory panel.
Solution A was described as: "salty"
Solution B was described as: "sweet", "lingering umami", "more salivating"
Solution C was described as: "sweet", "umami". 40% of the panel found this detectable.
Solution D was described as: "sweet", "umami". 100% of the panel found this detectable.

The strength of the taste of solutions B and D are comparable.

Example 5

Four different tomato soup powder compositions were prepared by dry mixing the ingredients as given in table 1.

TABLE 1

| Ingredients | A (Control) | B (50% reduced salt) | C (improved version) | D (improved version) |
|---|---|---|---|---|
| Potato starch | 16.9 (g) | 16.9 (g) | 16.9 (g) | 16.9 (g) |
| Tomato powder | 35 (g) | 35 (g) | 35 (g) | 35 (g) |
| Sugar | 10 (g) | 10 (g) | 10 (g) | 10 (g) |
| Fructose | 5 (g) | 5 (g) | 5 (g) | 5 (g) |
| Milk powder | 20 (g) | 20 (g) | 20 (g) | 20 (g) |
| Onion powder | 1.6 (g) | 1.6 (g) | 1.6 (g) | 1.6 (g) |
| Garlic powder | 0.1 (g) | 0.1 (g) | 0.1 (g) | 0.1 (g) |
| Carrot powder | 0.1 (g) | 0.1 (g) | 0.1 (g) | 0.1 (g) |
| MSG | 3.3 (g) | 3.3 (g) | 3.3 (g) | 3.3 (g) |
| Yeast extract | 1 (g) | 1 (g) | 1 (g) | 1 (g) |
| Salt | 7 (g) | 3.5 (g) | 3.5 (g) | 3.5 (g) |
| Maltodextrin |  | 3.5 (g) | 3.5 (g) | 3.5 (g) |
| Acetyl-GMP |  |  | 0.005 (mg) |  |
| Lactoyl-GMP |  |  |  | 0.3 (mg) |
| Total | 100 (g) | 100 (g) | 100 (g) |  |

10 Gram of each composition was mixed with 100 ml hot water to obtain tomato soups. The different soups were tasted and evaluated by a sensory panel. Product C, comprising acetyl-GMP as prepared in example 2, was clearly preferred over product B (50% salt reduction). Product D, comprising lactoyl-GMP was clearly preferred over product B (50% salt reduction). Despite the reduced salt content of products C and D, the perceived saltiness of the products was comparable to that of product A. Furthermore, the taste of products C and D was described as having "more taste", "more impact", "more kokumi", "long lasting" and "salivating".

Example 6

Three yoghurts were prepared according to the recipe in table 2.

TABLE 2

| Ingredients | Yoghurt A | Yoghurt B | Yoghurt C |
|---|---|---|---|
| Yoghurt, 0% fat | 100 (g) | 100 (g) | 100 (g) |
| Aspartam | 0.02 (g) | 0.02 (g) | 0.02 (g) |
| Acesulfam | 0.02 (g) | 0.02 (g) | 0.02 (g) |
| Acetyl-GMP |  | 0.003 (microgram) |  |
| Lactoyl-GMP |  |  | 0.15 (microgram) |
| Red fruit flavour | 0.1 (g) | 0.1 (g) | 0.1 (g) |

All products were tasted and evaluated by a sensory panel. Products B and C were clearly preferred over product A. Product A was described as sweet, fruity, berry-like, dull and slightly bitter, whereas products B and C were described as sweet, fuller, more natural berry-like, fruity and more balanced flavour. The strength of products B and C was comparable.

Example 7

Preparation of a Process Flavour

In a vessel 90 g acetic acid, 10 g water, 2.5 g dextrose and 5 g salt are combined and mixed by stirring. To this mixture 22.5 g GMP disodium salt is added. The mixture is stirred and heated at 100° C. for 4 hours. The mixture is cooled to room temperature and 25 g water is added resulting in a total of 155 g product. 120 g Water is added to 37.2 g of this product. The pH of this mixture is adjusted to 6 using 50% NaOH solution. 88.8 g Maltodextrin is dissolved in this mixture and the resulting solution is spraydried resulting in a final powder product.

Example 8

Process Flavour Evaluation

Three aqueous solutions were prepared:
A. 0.5% salt and 0.05% MSG
B. 0.2 ppm product as prepared in example 7 dissolved in solution A
C. 1 ppt product as prepared in example 2 dissolved in solution A The solutions were tasted by a professional sensory panel. Solution A was described as: "salty". Solution B was described as: "sweet", "umami". Solution C was described as: "sweet", "umami". The sensory effects of solutions B and C were comparable. The strength of solution B was slightly weaker than solution C.

Example 9

Preparation of an N-succinyl GMP Process Flavour

In a vessel 50 g succinic acid, 50 g water, 2.5 g dextrose and 5 g salt are combined and mixed by stirring. To this mixture 22.5 g GMP disodium is added. The mixture is stirred and heated at 100° C. for 4 hours. The mixture is cooled to room temperature and 25 g water is added resulting in a total of 155 g product. 120 g Water is added to 37.2 g of this product. The pH of this mixture is adjusted to 6 using 50% NaOH solution. 88.8 g Maltodextrin is dissolved in this mixture and the resulting solution is spraydried resulting in a final powder product.

Example 10

N-succinyl GMP Process Flavour Evaluation

Three aqueous solutions were prepared:
A. 0.5% salt and 0.05% MSG
B. 10 ppm product as prepared in example 9 dissolved in solution A
C. 50 ppm product as prepared in example 9 dissolved in solution A The solutions were tasted by a professional sensory panel. Solution A was described as: "salty" and "umami". Solution B was described as: "salivating", "umami", "salty", "long-lasting" and "bouillon-like". The perception of saltiness and umami in solution B was stronger than that in solution A.

Solution C was described as stronger than solution B but still pleasant, especially the saltiness was perceived to be sharper and stronger.

The invention claimed is:

1. Flavour modulating substances according to formula (I) as well as edible salts and esters thereof:

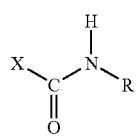

wherein X represents methyl;

wherein R represents a moiety comprising a bicyclic fused ring system comprising a five membered heterocyclic ring and a six membered heterocyclic ring, each ring comprising at least two nitrogen atoms, and the five membered heterocyclic ring being further substituted with a phosphate ester of ribose, wherein the moiety —NRH represents the residue of guanosine 5'-monophosphate (GMP).

2. Flavour modulating substance N-acetyl GMP, edible salts thereof and edible esters thereof.

3. Flavouring compositions comprising at least 60 ppt of one or more flavour modulating substances as defined in claim 2, as well as at least 0.1 wt % of one or more flavouring substances.

4. Product selected from the group of foodstuffs, beverages, pharmaceutics, oral care products and tobacco products, said product comprising a flavour modulating amount of one or more flavour modulating substances as defined in claim 1.

5. Product according to claim 4, wherein said flavour modulating amount is an amount of at least 0.3 ppt.

6. Method of improving the flavour of a product selected from the group of foodstuffs, beverages, pharmaceutics, oral care products and tobacco products, said method comprising incorporating in said product a flavour modulating amount of one or more flavour modulating substances as defined in claim 1.

7. Method according to claim 6, wherein said flavour modulating amount is an amount of at least 0.3 ppt.

8. Process of producing a process flavour preparation comprising heating a mixture of
    (i) a carbohydrate source;
    (ii) a nitrogen source, said nitrogen source comprising 0.5-100 wt %, of an amine represented by the formula $NH_2R$, wherein R represents a moiety comprising a bicyclic fused ring system comprising a five membered heterocyclic ring and a six membered heterocyclic ring, each ring comprising at least two nitrogen atoms, and the five membered heterocyclic ring being further substituted with a phosphate ester of ribose, wherein the moiety —NRH represents the residue of guanosine 5'-monophosphate (GMP); and
    (iii) one or more of carboxylic acids represented by formula (II) and/or salts thereof:

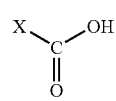

wherein X represents methyl.

9. Flavouring compositions comprising at least 60 ppt of one or more flavour modulating substances as defined in claim 1, as well as at least 0.1 wt % of one or more flavouring substances.

10. Product selected from the group of foodstuffs, beverages, pharmaceutics, oral care products and tobacco products, said product comprising a flavour modulating amount of one or more flavour modulating substances as defined in claim 2.

11. Product according to claim 10, wherein said flavour modulating amount is an amount of at least 0.3 ppt.

12. Method of improving the flavour of a product selected from the group of foodstuffs, beverages, pharmaceutics, oral care products and tobacco products, said method comprising incorporating in said product a flavour modulating amount of one or more flavour modulating substances as defined in claim 2.

13. Method according to claim 12, wherein said flavour modulating amount is an amount of at least 0.3 ppt.

* * * * *